United States Patent [19]

Lustig

[11] Patent Number: 4,579,532

[45] Date of Patent: Apr. 1, 1986

[54] DENTAL RETENTION PINS WITH PIN-HOLE SEALING AND PENETRATION STOPPING MEANS

[76] Inventor: Leopold P. Lustig, 304 Greenwood St., Newton Ctr., Mass. 02159

[21] Appl. No.: 695,054

[22] Filed: Jan. 25, 1985

[51] Int. Cl.⁴ ............................................. A61C 5/04
[52] U.S. Cl. .................................................. 433/225
[58] Field of Search ........................................ 433/225

[56] References Cited

U.S. PATENT DOCUMENTS 4,187,611  2/1980  Chan .................................. 433/225
4,449,937  5/1984  Weissman ........................... 433/225

FOREIGN PATENT DOCUMENTS 2468353  5/1981  France ............................... 433/225

Primary Examiner—Robert Peshock
Attorney, Agent, or Firm—Alfred H. Rosen

[57] ABSTRACT

A dental restorative pin is provided in three sequential sections, the first intended to penetrate into and to engage in a dentinal pin-hole having a hemispherical indentation surrounding its opening, a second section having a sealing surface curved on a hemispherical locus for mating with the hemispherical indentation when the first section penetrates into said pin-hole, to seal the opening, and to limit penetration of the first section into the pinhole, and the third section extending supragingivally from the second and being embeddable in a surrounding body of restorative material. Means is provided to form an annular open zone surrounding the junction of the first and second sections when the first section is engaged in the pin-hole and the sealing surface of the second section is mated to the hemispherical indentation.

9 Claims, 8 Drawing Figures

DENTAL RETENTION PINS WITH PIN-HOLE SEALING AND PENETRATION STOPPING MEANS

INTRODUCTION

This invention relates generally to dental retention pins intended for engagement in a tooth structure, for supporting dental restorative material. More particularly, dental retention pins according to the invention comprise, in series, a first pin-hole engaging section, an intermediate stop section having a sealing surface curved on a hemispherical locus for limiting penetration of the pin-hole engaging section and sealing the opening into the pin-hole, and a third section which extends supragingivally and is embeddable in a surrounding body of restorative material.

THE PRIOR ART

This invention is an improvement upon the invention of my prior application Ser. No. 262,305, filed May 11, 1981.

GENERAL NATURE OF THE INVENTION

A dental retention pin is provided which has, in series, three sections: a pinhole-engaging section for engagement in a pinhole bored to a prescribed depth through a surface of a damaged tooth, which pinhole has a hemispherical indentation surrounding its entrance opening; an intermediate stop section having a sealing surface for engagement in the hemispherical indentation and stopping penetration of the pin hole engaging section into said pinhole short of reaching the bottom of said pinhole, the pinhole-engaging section being shorter than the depth of the pinhole; and an upper section in the shape of a post extending supragingivally and embeddable in a surrounding body of restorative material. The stop section preferably has a truncating flat surface at the junction of the first and second sections, which forms with the hemispherical indentation an annular open space when the stop is seated in said entrance opening. Desirably, the third section may be flexurally connected to the second, intermediate section.

The present invention provides an improved stop component for dental pins which serves in an improved way both as a depth limiting device and a sealer for the bore in which the pinhole-engaging portion is mounted. The invention continues to use the depth-limiting feature, which is important in order to prevent splitting of tooth substances (dentin), which frequently occurs when pins which are stopped on the bottom of the bore according to the known prior art are used. Dentinal substance, however, is easily split, or otherwise damaged, in other locations, to which the present invention is addressed. Thus according to the invention, a spherical indentation surrounding the entrance to a pre-drilled bore provides a larger contact surface for a seal and stop section than does a frustro-conical surface; and a stop surface curved on the locus of a hemisphere distributes sealing forces over the larger surface. In addition, the invention further contemplates the provision of an annular open zone surrounding the junction of the hole-penetrating pin section and the stop section, thereby to relieve strain on the region of the tooth structure where the hole shape changes to the flared opening, and to provide a space to capture any debris that may remain after the hole has been drilled and cleaned. This annular open zone cooperates with a flushing passage provided, if desired, in the pin-hole engaging section.

DETAILED DESCRIPTION OF THE DRAWINGS

Figure 1:
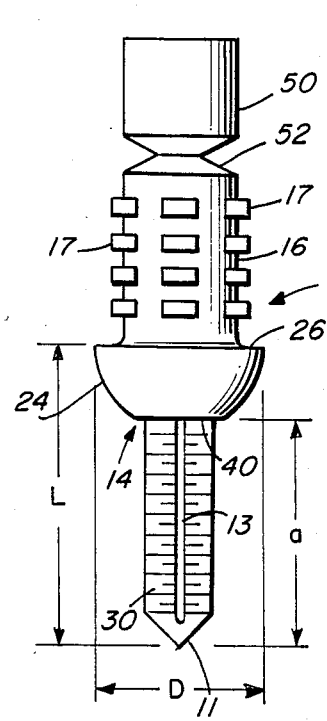
FIG. 1 illustrates a pin according to the invention.

The pin 10 has a first pin-hole engaging section 12, a stop secton 14 having a lower surface 24 curved on a hemispherical locus, and a top flat surface 26, and an upper supra-gingivally extending section 16. A pinhole 20 formed in dentinal tooth structure 18, through a wall 28 of a cavity (not shown) has a hemispherical indentation 22 surrounding its entrance opening 23. The first section 12 of the pin is engageable in the pinhole 20; it may be threaded (as illustrated at 30) or designed for cementing into the pinhole, or otherwise. Desirably, it has a flushing passage 13 returning along its outer surface. According to the invention, the length L from the top flat surface 26 to the extreme tip 11 of the first section 12 is shorter than the depth $L+\Delta L$ from the cavity wall 28 to the bottom 21 of the pinhole; and the length "a" of the first pin-hole engaging section 12 is shorter than the depth $a+\Delta a$ of the pinhole 20 measured from the bottom of the indentation 22. The stop section 14 therefore seats with its lower curved surface 24 on the curved surface of the indentation 22, limiting penetration of the first section 12 short of the bottom 21 of the pinhole. The hemispherical surface 24 is truncated by a flat surface 40 formed at the junction between the first section 12 and the stop sections 14, for a purpose to be described. The top flat surface 26 of the stop is ( in this embodiment) preferaby flush with the wall 28 when the stop section 14 is seated on the curved opening surface of the indentation 22. The upper section 16 is embeddable in a surrounding body (not shown) of restorative material, in any known manner. Preferably, the upper section 16 is fitted with means 17, for example, in the form of rectangular extensions for retaining a restorative material on it.

Pins according to the invention not only prevent injuring the tooth caused by impacting the bottom of prepared pinholes; they also stop penetration and seal the pinhole with precision. Owing to the increased contact surface provided by a hemispherical locus, as compared with the locus of a truncated cone, they are also more stable than, and can seal tighter than, pins having frustro-conical seals which enlarge to the same diameter D. In the present invention, the larger diameter D of the stop section 14 is greater than the crest diameter of threads 30 illustrated on the pin-hole engaging section 12. In the present invention, the two mating curved surfaces 22, 24 can meet closely with precision;

if the first lower section 12 is threaded, these two surfaces can be brought tightly together.

Figure 3:
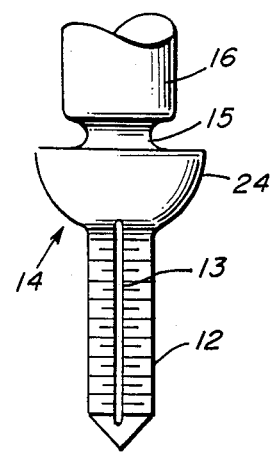
FIG. 3 shows another pin according to the invention.

In FIG. 3, the junction 15 between the upper, supragingival, section 16 and the stop section 14 is slightly narrower than the upper section, or otherwise treated so that the upper section 16 can be bent, or flexed relative to the stop section 14. The contours of this construction are smooth, and it has a round cross-section, so that it will resist shearing.

Figure 2:
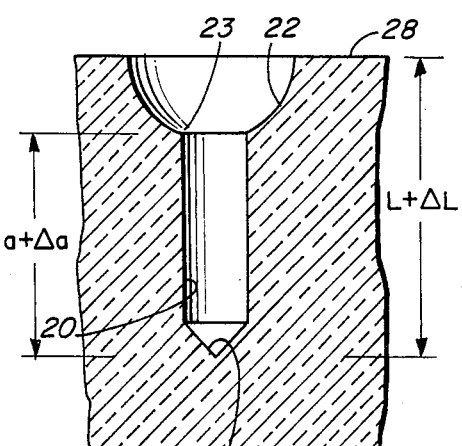
FIG. 2 illustrates a hole prepared in a tooth for a pin according to the invention.
Figure 4:
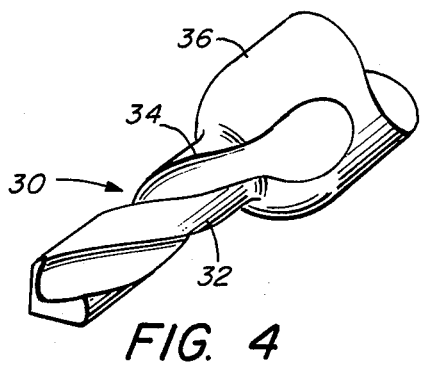
FIG. 4 shows a drill for preparing the hole of FIG. 2.

FIG. 4 shows a drill 30 having a hole-boring section 32 and an indentation forming section 34, for preparing the hole 20 and indentation 22 shown in FIG. 2. The shaft 36 can be engaged in any suitable dental engine, for drilling the hole.

Figure 5:
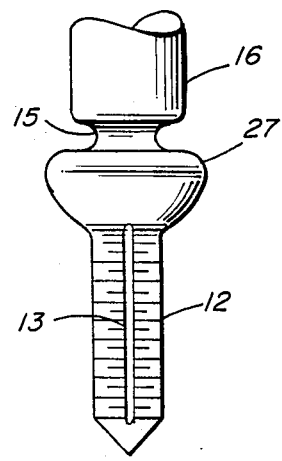
FIG. 5 shows still another pin according to the invention.

In FIG. 5, which is otherwise similar to FIG. 3, the top surface 27 of the stop section 14 is curved, with the flex section 15 at its center.

Figure 6:
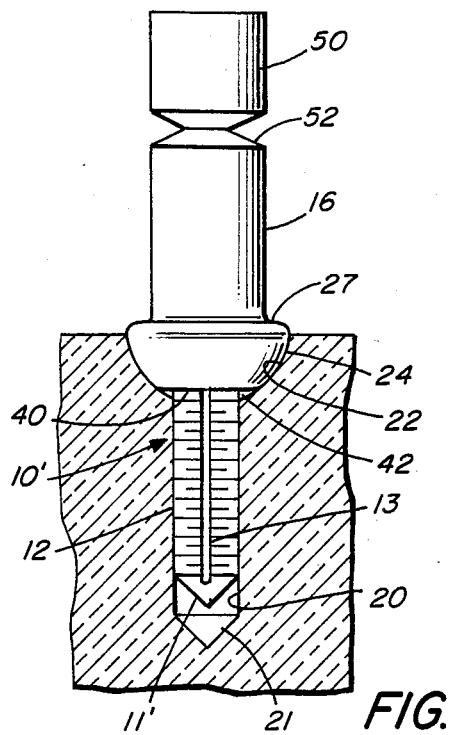
FIG. 6 illustrates a pin according to the invention seated in a hole previously prepared, as in FIG. 2.
Figure 6A:
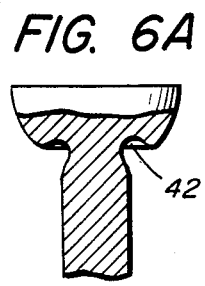
FIG. 6A shows a modification of a feature of the invention.

FIG. 6 illustrates a dental restorative pin installed in a prepared pin-hole in a tooth, according to the invention. As is illustrated FIG. 1, the hemispherically curved surface 24 is flattened at the junction 40 between the stop section 14 and the first hole-penetrating section 12, so that the hemispherically curved portion is slightly truncated, relative to the hemispherical locus of the indentation 22. When the stop section 14 is seated in the indentation 22, an annular open space 42 is left between the surface of the indentation and the surfaces of the pin where the lower hole-penetrating section 12 meets the stop section 14, thus preventing the exertion of force on the relatively sharp annular region of the dentinal material between the indentation 22 and the hole 20. This relatively sharp annular region is subject to fracture, which the present invention avoids. The annular open space 42 is useful also to capture any small piece or pieces of debris that may be left in the hole 20 after drilling in spite of the best efforts made to flush it out before inserting the pin section 12 into the hole, and cooperates with the flushing passage 13 for that purpose. As shown in FIG. 6A, the annular open space 42 can be further enlarged into the lower body of the stop section 14.

Figure 7:
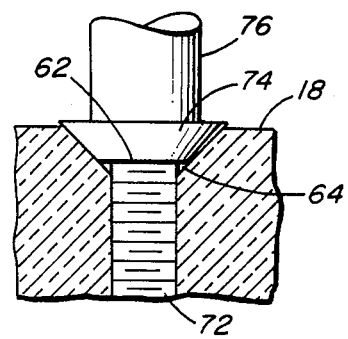
FIG. 7 illustrates a feature of the invention as applied to a pin according to my above-mentioned prior application.

FIG. 7 shows the same feature applied to a pin 72, 74, 76 having a frustro-conical sealing section 74 truncated at 62 to provide an annular open space 64. This feature is applicable to pins according to my prior pending application mentioned above.

The upper supragingival section 16 will be used to insert the lower section 12 into the pin hole 20, and, when the threads 30 are used, to turn the pin 10 so as to draw the lower section into the pinhole. As is well-known, a manipulating head 50 can be fitted to the upper section 16 via a break-away connection 52. Such break-away joints are old and well-known in the art of dental pins. According to the known prior art, it is the usual function of such a connection to break by reason of torsional failure when a screw-pin driven through it reaches the bottom of the pin hole into which the pin is being driven (screwed). The present invention transfers the "break-away" signal from the bottom 21 of the hole to the extended area hemispherical surface of the indentation 22. The flex section 15 (FIG. 3) resists shearing, so that it will not break before the break-away connection does.

I claim:

1. In combination with a dentinal pin, post or the like intended to be placed in a hole prepared in the dentinal portion of a damaged tooth for supporting a restoration of said tooth, a hemispherical depression formed in said tooth around said hole, and a sealing member having a sealing surface curved on a hemispherical locus on a substantially the same radius as said depression, a hole-penetrating post extending in one direction from the curved surface of said sealing member and a restoration-supporting post extending in an opposite direction from said sealing member, whereby when said hole-penetrating post is fitted into said hole said sealing member can be mated substantially uniformly with said depression and said sealing member, a flex portion of said pin adjacent the junction between said sealing member and said restoration-supporting post being smoothly contoured to a cross section that is narrower than the cross-section of said restoration-supporting post so that the latter can be flexed relative to said sealing member.

2. A combination according to claim 1 wherein said hole in said dentinal portion is prepared to a depth greater than the length of said hole-penetrating post, so that said sealing member will seal tightly in said depression while holding said post off the bottom of said hole.

3. A dental pin intended to be threaded into a hole prepared in the dentinal portion of a damaged tooth for supporting a restoration of said tooth, said pin comprising in sequence a threaded hole-penetrating section, a penetration-stop and sealing section and a restoration-supporting section, said penetration-stop and sealing section being re-entrantly apertured in an annular region surrounding its junction with said hole-penetrating section for providing an annular receiver of dental debris around said junction when said pin is fitted into said hole.

4. A dental pin according to claim 3 wherein said restoration-supporting section is flexurally attached to said penetration-stop and sealing section.

5. A dental pin according to claim 3 including an axially-oriented vent passage on the exterior of said hole-penetrating section, said vent passage communicating with said annular void.

6. A dentinal retention pin having, sequentially in a unitary structure, a longitudinally-extending lower shaft section of a first length for insertion into a prepared hole in the dentin of a tooth the depth of which is greater than said first length, an intermediate stop section of a larger cross-section than said shaft section for simultaneously limiting penetration of said shaft section into said hole and sealing the entrance to said hole, and an upper supra-gingivally extending restoration-supporting section which also provides a means to engage said shaft section in said hole, a flex portion of said pin adjacent the junction between said restoration-supporting section and said stop section being smoothly contoured to a cross-section that is narrower than the cross-section of said upper section so that said restoration-supporting section can be flexed relative to said stop section.

7. A pin according to claim 6 in which said lower shaft section is threaded for threaded insertion in said hole, and siad restoration-supporting section provides a means to rotate said pin through said flex portion for seating said stop section on said entrance, smooth contours of said flex portion providing to said flex portion the ability to resist fracture during seating of said stop section.

8. A pin according to claim 7 including a manipulative portion attached via a break-away joint to the free extremity of said restoration-supporting section, said break-away joint having the function to break by reason of torsional failure when said stop section is seated on said entrance without imposing an irresistible shearing force on said flex portion.

9. A pin according to claim 6 in which said pin-hole has a flared entrance, and said stop section has a lower surface which flares from the diameter of said lower shaft section to a larger diameter at its upper side adjacent said flex portion.

* * * * *